(12) United States Patent
Joyce et al.

(10) Patent No.: US 7,777,065 B2
(45) Date of Patent: *Aug. 17, 2010

(54) REMOVAL OF RESIDUAL SULFUR DIOXIDE FROM DIMETHYL SULFATE

(75) Inventors: William Francis Joyce, Hopewell Junction, NY (US); Jeffrey Earl Telschow, Croton-on-Hudson, NY (US)

(73) Assignee: Akzo Nobel N.V., Arnhem (NL)

( * ) Notice: Subject to any disclaimer, the term of this patent is extended or adjusted under 35 U.S.C. 154(b) by 70 days.

This patent is subject to a terminal disclaimer.

(21) Appl. No.: 11/885,202

(22) PCT Filed: Mar. 8, 2006

(86) PCT No.: PCT/EP2006/060545

§ 371 (c)(1),
(2), (4) Date: Aug. 28, 2007

(87) PCT Pub. No.: WO2006/097421

PCT Pub. Date: Sep. 21, 2006

(65) Prior Publication Data

US 2008/0207940 A1    Aug. 28, 2008

Related U.S. Application Data

(60) Provisional application No. 60/661,366, filed on Mar. 14, 2005.

(51) Int. Cl.
 C07C 303/00 (2006.01)
(52) U.S. Cl. ....................................... 558/43
(58) Field of Classification Search ............. 558/43
See application file for complete search history.

(56) References Cited

U.S. PATENT DOCUMENTS

| 4,830,771 A | 5/1989 | Ruback et al. |
| 5,670,677 A | 9/1997 | Ponsati Obiols et al. |
| 7,326,814 B2 * | 2/2008 | Band et al. ............. 564/296 |

FOREIGN PATENT DOCUMENTS

| DE | 41 21 409 A1 | 1/1993 |
| DE | 101 32 526 A1 | 1/2003 |
| GB | 119250 | 9/1918 |
| WO | WO 2004/060854 A1 | 7/2007 |

OTHER PUBLICATIONS

International Search Report for International Application No. PCT/EP2006/060545, Aug. 18, 2006.
Derwent Abstract No. 93-018842/03 for German Patent Application No. 4121409A1, 1993.
Derwent Abstract No. 2003-269688/27 for German Patent Application No. 10132526A1, 2003.

* cited by examiner

*Primary Examiner*—Rei-tsang Shiao
(74) *Attorney, Agent, or Firm*—Ralph J. Mancini

(57) ABSTRACT

The present invention relates to a method of removing $SO_2$ contaminants from dimethyl sulfate (DMS) by treatment with an oxidizing agent, and to a process for the preparation of odor free fatty acid trialkanolamine esters quaternized with DMS which is substantially free of $SO_2$ contaminants.

10 Claims, No Drawings

REMOVAL OF RESIDUAL SULFUR DIOXIDE FROM DIMETHYL SULFATE

FIELD OF THE INVENTION

The present invention generally relates to a process for the minimization and/or removal of sulfur dioxide from dimethyl sulfate.

BACKGROUND OF THE INVENTION

Quaternized fatty acid triethanolamine ester salts are cationic surfactants that are excellent fabric softeners that have high ecotoxicological compatibility. Ester quats are typically produced in a two-stage process in which triethanolamine is first partly esterified with fatty acids and the reaction product is subsequently quaternized with an alkylating agent. Hypophosphorous acid and sodium hypophosphite are preferred catalysts for the esterification step. However, during working up, particularly at relatively high temperatures, certain by-products are formed, resulting in an adverse effect on the odor of the dimethyl sulfate (DMS) quaternized product. Many of these odor-related problems can be traced to sulfur dioxide contaminants in the dimethyl sulfate. Accordingly, it is desirable to minimize and/or remove all of the sulfur dioxide from dimethyl sulfate prior to quaternization.

Accordingly, the invention provides a process for the minimization and/or removal of sulfur dioxide from dimethyl sulfate. When used in the quaternization of amines made with hypophosphorous acid, dimethyl sulfate having little to no sulfur dioxide leads to the formation of a product substantially free of malodors.

DETAILED DESCRIPTION OF THE INVENTION

The invention relates to a method of removing $SO_2$ contaminants from DMS, to an $SO_2$-free DMS and to odor-free products produced by said $SO_2$-free DMS.

Quaternized fatty acid triethanolamine ester salts are cationic surfactants that are excellent fabric-softeners that have high ecotoxicological compatibility. Ester quats are typically produced in a two-stage process in which triethanolamine is first partly esterified with fatty acids, and the reaction product is subsequently quaternized with an alkylating agent. Hypophosphorous acid and sodium hypophosphite are preferred catalysts for the esterification step. However, during working up, particularly at relatively high temperatures, certain by-products are formed, resulting in an adverse effect on the odor of the dimethyl sulfate-quaternized product. Many of these odor-related problems can be traced to sulfur dioxide contaminants in the dimethyl sulfate. Sulfur dioxide is a contaminant in commercial dimethyl sulfate in quantities ranging from a few tens of ppm to about 1000 ppm, and it is believed that malodor is due to methylated sulfur compounds produced in complex chemistry involving residues of reactive ingredients interacting in the final quaternization step. Since the methylated sulfur compounds are detectable by smell in quantities down to about 1 ppb, prevention of their formation is the most practical way to insure that DMS-quaternized esterquats are free of objectionable odors.

The invention provides a process for the minimization and/or removal of sulfur dioxide contaminants from dimethyl sulfate. The method involves addition of one or more oxidizing agents to convert the $SO_2$ contaminants in DMS effectively to $SO_3$ (or sulfuric acid derivatives). More specifically, the present inventors have demonstrated that DMS containing high levels of $SO_2$ produced high concentrations of methyl-S compounds as analyzed by GC. After treatment of the DMS by addition of one or more oxidizing agents such as t-butyl hydroperoxide and/or hydrogen peroxide in calculated quantities down to about an 18% excess, or less, in order to remove $SO_2$ contaminants from DMS the methyl-S compounds were no longer detectable by GC after quaternization.

The oxidizing agents employable in the process of the present invention include, but are not limited by agents of the formula: ROOR where R=H or $R'[O]_m[CO]_n$—, wherein R'=alkyl or aryl and m and n=0 or 1, with m=0 if n=0. Preferred oxidizing agents are peroxides, including but not limited to hydrogen peroxide, hydroperoxides, peroxides, peresters, percarbonates and the like. Specific examples of preferred oxidizing agents include, but are not limited to $O_2$, $O_3$, $Cl_2$, $KMnO_4$, $K_2Cr_2O_7$, $KClO_3$, $NaClO_2$, $HNO_3$, $H_2O_2$, t-butyl hydroperoxide, and the like.

The oxidizing agent(s) are added to the $SO_2$-containing DMS in quantities of from about 5 ppm to about 1000 ppm; in most cases in an amount of from about 10% to about 100% molar excess versus the analyzed molar amount of $SO_2$ will suffice. In another embodiment, an amount of from about 10% to about 100% molar excess versus the analyzed molar amount of $SO_2$ is employed. This treatment step is typically performed at room temperature, and subsequent to adding the oxidizing agent to the DMS, the DMS is allowed to stand from a few minutes up to a few hours.

The present inventors have also discovered a process for the production of products free of malodors when prepared from the dimethyl sulfate quaternization of amines made with hypophosphorous acid. In such products the volatile organic sulfur by-products that lead to the formation of objectionable odors are minimized. In this regard the invention comprises quaternizing said amines with a dimethyl sulfate quaternization agent wherein said dimethyl sulfate has a sulfur dioxide content of less than 10 parts per million (ppm), preferably less than 8 ppm, and still more preferably less than 5 ppm. Minimizing the sulfur dioxide content in the dimethyl sulfate quaternization agent reduces or eliminates the formation of undesirable odor-causing by-products such as hydrogen sulfide, methyl mercaptan, dimethyl sulfide and dimethyl disulfide, resulting in a greatly improved odor profile of the final product. The present invention is not limited to processes for the preparation of ester quats but rather, is applicable to any dimethyl sulfate quaternization process of amines made with esterification catalyst/reductive bleaching agents.

The esterification catalyst/reductive bleaching agents employed in the context of the present invention are characterized in that they typically have a standard reduction potential of at least 0.5 volts. Nonlimiting examples of such esterification catalyst/reductive bleaching agents are hypophosphorous acid, sodium hypophosphite and mixtures thereof.

In another embodiment, the present invention relates to quaternary ammonium compounds having particularly good performance and stability profiles obtained by reaction of $C_{12}$-$C_{22}$ fatty acids or the hydrogenation products thereof, or a mixture of such acids, with an alkanolamine in the presence of an acid catalyst, wherein the ratio of fatty acid to alkanolamine is from about 1.40-2.0. The resultant esteramine reaction products are subsequently quaternized to obtain the quaternary ammonium salts of the present invention.

The fatty acid is preferably a $C_{12}$-$C_{22}$ acid containing a degree of unsaturation such that the iodine value ("IV") is in the range of from about 0-140, preferably, from about 3-90, more preferably in the range of 40-60 and still more preferably, in a range of from about 45-55. Preferably, the fatty acid source is selected from $C_{12}$-$C_{22}$ fatty acids represented by the formula:

$$R_x\text{—COOH},$$

wherein, $R_x$ is a straight or branched chain $C_{11}$-$C_{21}$ alkyl group.

Preferred sources of $C_{12}$-$C_{22}$ fatty acids are selected from the group consisting of: lauric acid, tridecylic acid, myristic acid, pentadecylic acid, palmitic acid, margaric acid, stearic acid, arachidic acid, phytanic acid, behenic acid, anionic derivatives thereof, salts thereof, and combinations thereof.

Preferred sources of acid are $C_{12}$-$C_{22}$ fatty acids comprising a saturated alkyl group. Other preferred sources of acids are $C_{12}$-$C_{22}$ fatty acids comprising an unsaturated group, typically having an iodine value of from 15 to 25, preferably from 18 to 22.

The source of acid may be selected from the group consisting of palmitoleic acid, oleic acid, elaidic acid, vaccenic acid, linoleic acid, cis-eleostearic acid, trans-eleostearic acid, linolenic acid, arachidonic acid, anionic derivatives thereof, salts thereof, and combinations thereof.

Preferred sources of fatty acids are selected from the group consisting of coconut, soybean, tallow, palm, palm kernel, rapeseed, lard, sunflower, corn, safflower, canola, olive, peanut, and combinations thereof. A preferred source of acid is hard tallow fatty acid and/or partially hydrogenated tallow fatty acid.

Preferred fatty acids include but are not limited to oleic, palmitic, erucic, eicosanoic and mixtures thereof. Soy, tallow, palm, palm kernel, rape seed, lard, mixtures thereof and the like are typical sources for fatty acid which can be employed in the present invention. The fatty acid(s) employed in the present process optionally have a cis to trans isomer ratio of from about 80:20 to about 95:5. In another embodiment, the trans isomer content of said fatty acid(s) is less than about 10%. A typical trans-isomer content is between about 0.5-9.9%. A preferred fatty acid is a mixture of tallow/distilled tallow having a cis:trans isomer ratio of greater than 9:1. Partial or fully hydrogenated fatty acids can be employed in the process of the present invention.

The alkanolamines employable in the present invention generally correspond to the formula:

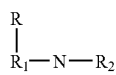

herein R, $R_1$ and $R_2$ are independently selected from $C_2$-$C_6$ hydroxyalkyl groups or a group of the formula

where $R_3$ is independently H or a $C_1$ to $C_4$ alkyl and z is 1 to 10.

Alternatively, the alkanolamines can be of the formula:

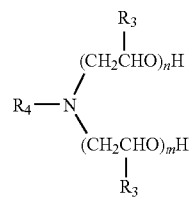

Where $R_4$ is a linear or branched, substituted or unsubstituted alkyl group, amidoalkyl group, etheralkyl group, or polyoxyalkylene group, n and m=1-10, and $R_3$ has the meanings defined above.

Examples of alkanolamines useful in the context of the present invention include, but are not limited to, triethanolamine, isopropanoldiethanolamine, ethanoldiisopropanolamine, triisopropanolamine, diethanolisopropanolamine, diethanolisobutanolamine, methyldiethanolamine and mixtures thereof.

The molar ratio of fatty acid to alkanolamine is generally in the range of from about 1.4 to 2.0, preferably from about 1.55-1.90, and more preferably, in the range of from about 1.65-1.75. Best results are usually obtained when the molar ratio is between about 1.68-1.72. The acid catalyst employable in the present process includes, but is not limited to, acid catalysts such as sulfuric acid, phosphorous acid, p-toluenesulfonic acid, methanesulfonic acid, oxalic acid, hypophosphorous acid or an acceptable Lewis acid in an amount of 500-3000 ppm based on the amount of fatty acid charge. A preferred acid catalyst is hypophosphorous acid. Typically, 0.02-0.2% by weight, and more preferably 0.1 to 0.15% by weight of acid catalyst, based on the weight of fatty acid, in employed in the present process.

The esterification of fatty acids with alkanolamines is carried out at a temperature of from about 150°-250° C. until the reaction product has an acid value of below 5. After the esterification, the crude product is reacted with alkylating agents in order to obtain the quaternary ammonium product. The alkylating agent employed in the present invention is dimethyl sulfate having a sulfur dioxide content of less than about 10 ppm. Typically, 0.7 to 1.0, preferably 0.75 to 0.98 mole of dimethyl sulfate per mole of esteramine is satisfactory in yielding the quaternized product.

The quaternization may be carried out in bulk or in solvent, at temperatures ranging from 60°-120° C. If a solvent is employed, then the starting materials and/or product must be soluble in the solvent to the extent necessary for the reaction. Solvents of this type are generally known in the art. Suitable examples include polar solvents such as, for example, lower alcohols, i.e., $C_1$-$C_6$ alcohols. Other solvents which can be employed include, but are not limited to mono-, di-, and tri-glycerides, fatty acids, glycols and mixtures thereof.

The products of the invention can beneficially be employed in textile softening and/or personal care compositions and in other applications typical for cationic surfactants.

The invention will now be illustrated by the following nonlimiting examples.

Example 1

In small vials, 5 mL portions of commercial DMS were treated with 50 μL portions of either water or an oxidizing agent, stirred 30 min and then sampled.

The SO$_2$ content was measured before and after treatment, as shown in the table.

DMS Treatments to Remove SO$_2$

| Additive | Mol/mol SO$_2$ | SO$_2$ Conc. µg/mL |
|---|---|---|
| none | — | 445 |
| water | 80 | 310 |
| 30% H$_2$O$_2$ | 14 | <3 (ND) |
| 70% t-BuOOH | 5.9 | <3 (ND) |

ND = not detected

Example 2

13.2 g of DMS containing roughly 2460 ppm SO$_2$ (0.51 mmol) was treated with 26 µL (~33 mg, 0.69 mmol, ~35% excess) of 71.1% H$_2$O$_2$ (d 1.285). The colorless solution had no detectable remaining SO$_2$.

Example 3

Hardened tallow triethanol ester methyl amine (HT TEEMA) was prepared using 1660 ppm (vs. fatty acid) of 50% hypophosphorous acid. Three 250-lb batches of hardened tallow triethanolamine ester quaternary (HT TEQ) were made by quaternization of the HT TEEMA with the following DMS feedstocks:
1. Commercial DMS containing ~80 ppm of SO$_2$.
2. Thirty-six pounds of DMS doped with 0.054 lb of sulfur dioxide to ~1500 ppm of SO$_2$.
3. Thirty-six pounds of DMS doped with ~1500 ppm of SO$_2$ and then treated with 0.086 lb, a 45-55% molar excess, of 50% hydrogen peroxide (~2400 ppm) to reduce the SO$_2$ to ~1 ppm (as analyzed after 4.5 hr). The excess peroxide corresponds to stoichiometry for the reaction: H$_2$O$_2$+ SO$_2$→H$_2$SO$_4$.

The reactor was washed thoroughly between batches to avoid potential cross-contamination. All of the HT TEQ samples were kept in a freezer to preserve the odor characteristics of each of the batches until all of the runs were completed. The HT TEQ samples were then evaluated by a formal, 6-person odor panel.

Both HT TEQ batches 3256 and 3257, made from DMS with 80 ppm and 1500 ppm of SO$_2$, respectively, had typical sulfur compound odors, with the latter batch having an exceptionally foul odor. The odor panel verified that the HT TEQ made from batch 3258 of treated DMS containing ~1 ppm SO$_2$ did not have any detectable sulfur type odors.

Analysis of HT TEQ Made on 250-lb Scale

| Sample (Batch #) | DMS Used # | SO$_2$ Conc. | CH$_3$SH | (CH$_3$)$_2$S | (CH$_3$)$_2$S$_2$ | Unk.[1] |
|---|---|---|---|---|---|---|
| | | | Nanograms/gram or ppb | | | |
| 3256 | 1 | 80 ppm | 3 | <2 | <2 | 1 |
| 3257 | 2 | 1500 ppm | 29 | 32 | 1423 | 7 |
| 3258 | 3 | 1 ppm | <2 | <2 | <2 | <2 |

We claim:

1. A process for removing residual SO$_2$ from dimethyl sulfate that comprises treating said dimethyl sulfate with an SO$_2$-removing effective amount of at least one oxidizing agent for a time and at a temperature effective to remove substantially all residual SO$_2$ from the dimethyl sulfate.

2. The process of claim 1 wherein said oxidizing agent is represented by the formula: ROOR where R=H or R'[O]$_m$[CO]$_n$—, wherein R'=alkyl or aryl and m and n=0 or 1, with m=0 if n=0.

3. The process of claim 2 wherein said oxidizing agent is selected from the group consisting essentially of hydrogen peroxide, hydroperoxides, peroxides, peresters, percarbonates and mixtures thereof.

4. The process of claim 3 wherein said oxidizing agent is selected from the group consisting essentially of O$_2$, O$_3$, Cl$_2$, KMnO$_4$, K$_2$Cr$_2$O$_7$, KClO$_3$, NaClO$_2$, HNO$_3$, H$_2$O$_2$, t-butyl hydroperoxide, and mixtures thereof.

5. The process of claim 1 wherein said oxidizing agent(s) are added to the SO$_2$-containing DMS in quantities of from about 5 ppm to about 1000 ppm.

6. The process of claim 5 wherein said oxidizing agent is added to said SO$_2$-containing DMS in an amount of from about 10% to about 100% molar excess versus the analyzed molar amount of SO$_2$.

7. The process of claim 1 wherein said treatment is conducted at ambient temperature.

8. The process of claim 1 wherein said dimethyl sulfate contains less than 20 ppm sulfur dioxide subsequent to said treatment.

9. The process of claim 8 wherein said dimethyl sulfate contains less than 8 ppm sulfur dioxide subsequent to said treatment.

10. The process of claim 9 wherein said dimethyl sulfate contains less than 5 ppm sulfur dioxide subsequent to said treatment.

* * * * *